United States Patent [19]

Miedaner

[11] 3,993,835
[45] Nov. 23, 1976

[54] TRANSITION METAL OXIDE COMPLEX COUPLING AGENTS COATED ON SILICEOUS SUBSTRATES

[75] Inventor: Patrick M. Miedaner, Aspinwall, Pa.

[73] Assignee: PPG Industries, Inc., Pittsburgh, Pa.

[22] Filed: Dec. 4, 1973

[21] Appl. No.: 421,705

Related U.S. Application Data

[63] Continuation of Ser. No. 208,238, Dec. 15, 1971, abandoned, which is a continuation of Ser. No. 836,889, June 26, 1969, abandoned.

[52] U.S. Cl. .............................. 428/378; 260/42.14; 260/42.16; 260/429.5; 260/438.5 R; 427/384; 427/385 R; 427/385 A; 427/407 R; 427/407 A; 427/407 B; 427/419 D; 427/419 G; 428/380; 428/384; 428/389; 428/390; 428/392; 428/432; 428/446; 428/524

[51] Int. Cl.² ................ B32B 17/02; B32B 17/06; C07F 7/28; C07F 11/00

[58] Field of Search ................ 260/438.5 R, 429.5, 260/42.14, 42.16, 524; 117/72, 123 C, 124 D, 126 GQ, 126 GF, 124 T, 62.1, 69, 120 GB, 124 E, 62, 123 B, 123 D, 124 B, 76 T, 118; 427/384, 385, 407, 419; 428/378, 392, 432, 446, 389, 390, 380, 384

[56] References Cited

UNITED STATES PATENTS

| | | | |
|---|---|---|---|
| 2,838,418 | 6/1958 | Storkweather | 117/126 GB |
| 2,938,812 | 5/1960 | Morzocchi | 117/126 GB |
| 2,941,903 | 6/1960 | Winston | 117/124 T |
| 2,999,768 | 9/1961 | Boresch | 117/152 X |
| 3,082,183 | 3/1963 | Boyd | 117/126 X |
| 3,161,531 | 12/1964 | Dettre et al. | 117/62 |
| 3,161,536 | 12/1964 | Dettre et al. | 117/124 |
| 3,261,736 | 7/1969 | Eilerman | 117/126 GB |
| 3,306,918 | 2/1967 | Schenck | 117/124 |
| 3,355,314 | 11/1967 | Gagnon | 117/126 |
| 3,379,556 | 4/1968 | Chiecchi | 117/123 |
| 3,402,064 | 9/1968 | Morzocchi | 117/126 GB |
| 3,413,186 | 11/1968 | Morzocchi | 117/126 GB |
| 3,484,271 | 12/1969 | Kaliski et al. | 117/62.1 |
| 3,617,162 | 11/1971 | Jane | 8/8 |
| 3,705,075 | 12/1972 | Morzocchi | 117/126 GB |

OTHER PUBLICATIONS

Diserens, Louis, Chemical Technology of Dyeing and Printing, New York, 1948, pp. 424–425.

*Primary Examiner*—William H. Schmidt
*Attorney, Agent, or Firm*—John E. Curley; Robert DeMajistre

[57] ABSTRACT

A substrate such as glass contains a coating of a transition metal oxide complex with an ortho functional aromatic compound which contains a functional group which can react with a phenolic or resorcinolic resin or other organic compound or polymer. The ortho functional aromatic compound can also be a phenolic or resorcinolic resin. The complex serves as a coupling agent between the substrate and the organic material. These coupling agents can be resinous coatings or they can be coatings which serve as a coupling agent type of composition for rendering the surfaces of the substrates more substantive or reactive to organic materials. The coatings are inorganic-organic complexes of a transition metal oxide or a hydroxide with an ortho functional aromatic compound. The aromatic compound can contain at least two functional groups in ortho position to each other and a functional group for interfacing or reacting with the organic material.

20 Claims, 1 Drawing Figure

F = FUNCTIONAL GROUP REACTIVE WITH ORGANIC MATERIAL

SUBSTRATE

F = FUNCTIONAL GROUP
REACTIVE WITH ORGANIC MATERIAL
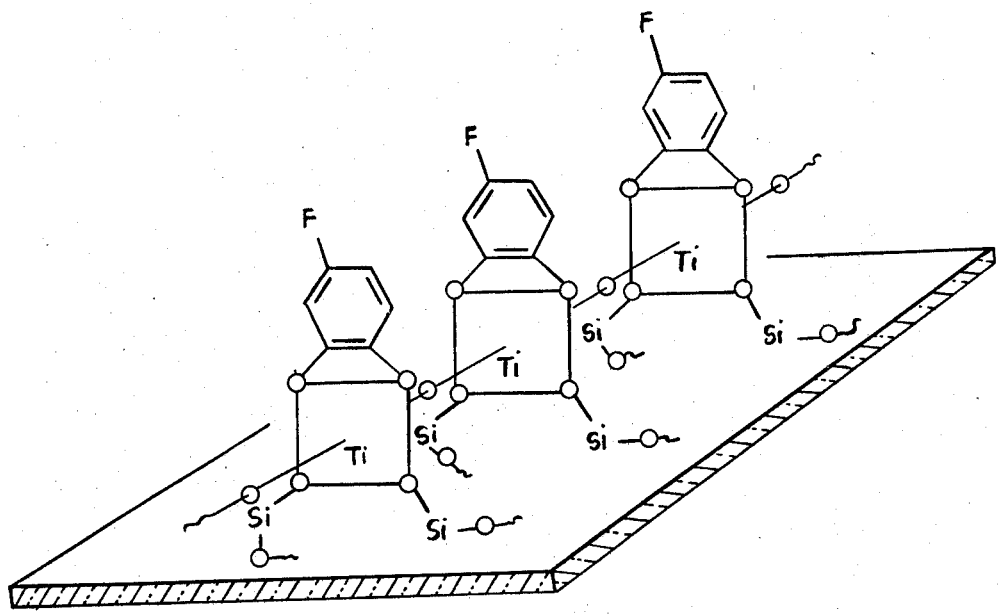
SUBSTRATE

TRANSITION METAL OXIDE COMPLEX COUPLING AGENTS COATED ON SILICEOUS SUBSTRATES

This is a continuation of application Ser. No. 208,238, filed Dec. 15, 1971 now abandoned, which is a continuation of application Ser. No. 836,889, filed June 26, 1969, now abandoned.

BACKGROUND OF THE INVENTION

1. Field of the Invention

The present invention relates to coating compositions and it has particular relation to coating compositions which render surfaces such as glass chemically reactive with organic compounds and polymers. More particularly, the invention relates to coating compositions which are applied to glass fibers during their forming into a strand which is to be used as a reinforcement for resinous and elastomeric products. These compositions have come to be known in the glass fiber art as "coupling agents".

The invention is described in particular relation to the manufacture and use of glass fibers; however, the invention is applicable to the coating of any material which normally has a highly polar surface, such as an oxide-containing or hydroxyl-containing surface. The hydroxyl groups may be part of the chemical composition of the material or they may be present as bound hydroxyl groups which are normally present on the surface of glass or siliceous articles.

2. Description of the Prior Art

A glass fiber strand is composed of a multitude of fine glass filaments which are formed by being drawn at a high rate of speed from molten cones of glass located at the tips of small orifices in a bushing such as shown in U.S. Pat. No. 2,133,238. During formation, the filaments are coated while moving at a speed in excess of 5,000 up to 20,000 feet per minute with a size which contains a binder to give the strand integrity for workability for any standard textile or reinforcement use. If the strand does not have proper integrity, fuzzing occurs during these operations and eventually the strand breaks. The size also contains a lubricant for the filaments to prevent destruction of the strand by abrasion of the individual filaments against each other or against fiber handling equipment.

It is common practice to use glass fiber strands and glass fiber cloth as a reinforcement for resins. For such use, the glass fibers are coated with a coupling agent or finish material which makes the surface of the glass fibers substantive and compatible with the particular resins with which they are to be employed. These coupling agents greatly increase the dry and wet physical strengths of the glass fiber resin laminate.

When the glass fibers are used in the form of strand, i.e., roving or chopped strand or twisted strand, for resin reinforcement, the coupling agent is usually combined with the size and applied with the size to the fibers during their formation. The size employed is usually an aqueous dispersion of a film forming, synthetic binder, and a glass fiber lubricant.

Coupling agents which have been used in aqueous size compositions in the prior art include silane and siloxane materials. For example, hydrolyzable vinyl, allyl, beta chloropropyl, phenyl, thio-alkyl, thio-alkaryl, amino-alkyl, methacrylato, epoxy and mercapto silanes, their hydrolysis products and polymers of the hydrolysis products and mixtures of any of these are suitable for such use. Some of the silanes are disclosed in U.S. Pat. Nos. 2,563,288; 2,688,006; 2,688,007; 2,723,211; 2,742,378; 2,754,237; 2,776,910; 2,799,598; 2,832,754; 2,930,809; 2,946,701; 2,952,576; 2,974,062; 3,044,982; 3,045,036; 3,169,884; 3,207,623 and 3,211,684.

Another class of coupling agents which has been found to be useful are the basic (hydroxy containing) metal salts of a strong mineral acid, such as, for example, a basic chromium chloride, basic chromium sulfate, etc. These compounds are ones having a trivalent metal ion selected from the group consisting of chromium, cobalt, nickel, copper and lead, at least one hydroxyl group attached to the metal, and at least one anion of a strong mineral acid attached to the metal (as well as coordinate complexes of these compounds and mixtures thereof).

Another type of coupling agent which has been used is a complex compound of the Werner type in which a trivalent nuclear atom, such as chromium, is coordinated with an organic acid such as methacrylic acid, i.e., a methacrylic acid complex of chromic chloride. Such agents are described in U.S. Pat. No. 2,611,718. Other Werner type coupling agents having vinyl, alkyl, amino, epoxy, mercapto, thio-alkyl, thio-alkaryl, and phenyl groups are suitable for use.

Mixtures of two or more of any of these coupling agents have been used.

Roving is formed by combining a number of strands in parallel form and winding the strands on a tubular support in a manner such that the combined strands may be unwound and used to form woven roving or chopped strands. Twisted strand (singe end on a bobbin) is made according to conventional textile twisting techniques by removing the strand from the forming package and winding it on a twister bobbin. It is therefore necessary that the strand have good integrity and resistance to fuzzing during the steps employed to make the twisted strand or roving and fabricate them into forms suitable for use as a resin reinforcement.

It is desired that a treatment be provided for glass fiber strand which will render the strand capable of providing increased strength to glass fiber reinforced resinous and elastomeric products. For example, it is desired that a strand be provided which is equally useful as a reinforcement for styrenated polyester resins, epoxy resins, thermoplastic resins, natural rubber and synthetic rubbery polymers. In this regard it is desired to produce a strand which is composed of a plurality of smaller or fine strands which are easily wet-out with resin or coated or impregnated with a rubber adhesive coating.

It is an object of this invention to provide an elastomer (rubber) coated glass fiber strand, yarn, roving or textile fabric for reinforcement of elastomers (rubber). The elastomer (rubber) coated glass fiber reinforcement should adhere well to the elastomer matrix at high and low temperatures and should have long life and good strength under severe flexing conditions.

The term "elastomer" as used herein and in the claims is intended to include elastic substances such as natural latex from the Hevea tree and synthetic rubber and rubber-like materials. It also includes natural and synthetic rubber and rubber-like materials which have been chemically modified such as by chlorination to improve their physical properties. Synthetic rubber includes rubber-like materials such as chloroprene, butadiene, isoprene and copolymers thereof with acrylonitrile, styrene and isobutylene. The term "elastomer" includes natural and synthetic rubber in the uncured or unvulcanized state as well as in the cured or vulcanized state.

SUMMARY OF THE INVENTION

According to the present invention, hydrolytically stable organic coatings are obtained on the surfaces of substrates. These coatings can be resinous coatings or they can be coatings which serve as a coupling agent type of composition for rendering the surfaces of the substrates more substantive or reactive to organic materials. The coatings are inorganic-organic complexes of a transition metal oxide or hydroxide and an ortho functional aromatic compound. It can be an aromatic compound containing (1) at least two functional groups in ortho position to each other and (2) a functional group for interfacing or reacting with the organic material. The aromatic compound can also be a phenolic or resorcinolic resin.

BRIEF DESCRIPTION OF FIRGURES

The FIGURE illustrates the manner in which inorganic-organic complex interfaces with the surface of the substrate by virtue of a metal-oxygen linkage.

DETAILED DESCRIPTION OF THE INVENTION

The coating can be built up step-wise on the surface of the substrate or it can be partially or fully formed and then applied to the surface. For exmple, a metal oxide film on the surface can be complexed with the polyfunctional aromatic compound, or the complex can be produced separately and applied to the base as an aqueous solution or dispersion. The coating provides improved properties to products whose surfaces are contacted by organic coatings or which serve as reinforcements or fillers in organic matrixes.

The metal elements whose oxides or hydroxides are useful in the practice of the present invention are the transition metal elements, preferably having atomic numbers from 21 to 40 inclusive with titanium, iron, chromium and zirconium being typical examples of the preferred metal elements. These elements have d-orbitals which are available for complexing with ligand donor groups. The metal is chosen so that the complex is hydrolytically stable when situated on the surface of the substrate.

The aromatic polyfunctional compounds which are useful in the practice of the invention are of three general types having the following basic chemical structures:

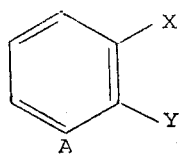
A

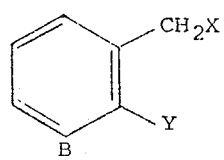
B

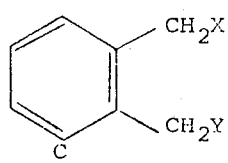
C wherein X and Y can be functional groups having unshared electrons such as OH, $NH_2$, Cl, Br, CN and SCN. These compounds, when complexed with the transition metal oxide form respectively 5, 6 and 7 member complex rings.

The aromatic polyfunctional compounds may also have additional functional groups attached to the aromatic ring to permit reaction of the complexes with various organic materials. The additional functional groups include amine, imine, polyamine, polyimine, chloro-containing, thio-containing, olefinic-containing, epoxy-containing, hydroxyl-containing, or any other desired functional group.

The invention can be described with regard to the coating of substrates with phenolic ore resorcinolic resins as the organic material. The substrate first can be coated with the transition metal oxide. The transition metal oxide can be complexed with a type A ortho functional aromatic compound provided with amine groups to form a coupling agent for reaction with the phenolic resorcinolic resin, or the transition metal oxide can be complexed directly with the phenolic or resorcinolic resin without the need for forming the coupling agent. The phenolic and resorcinolic resins are examples of the type B ortho functional aromatic group and thus, can complex directly to the transition metal oxide.

The direct complexing of the resin to the transition metal oxide on the substrate is more economical since it eliminates the step of forming the coupling agent. The best coating economics in either case are obtained if the complex is separately formed and then applied to the substrate.

When the coupling agent is formed, the preferred aromatic polyfunctional compound is an ortho-dihydroxy phenyl compound having various functional groups attached to the phenyl radical. Examples of these compounds are catechualdehyde and αchloro-3,4-dihydroxy acetophenone. These compounds can be reacted with amine compounds by Mannich reaction to provide them with amine groups for reaction with organic materials.

Although the utility of the invention does not depend on the theory of the invention, the following is offered as an explanation of what occurs in the practice of the invention when titanium is used as the metal element. Non-ionized titanium has four valence electrons. These electrons reside in two sub-shells, i.e., the $4s$ and $3d$ levels and constitute the primary or ionic valences of the atom. Since the electrons reside in the third and fourth quantum levels, they are a considerable distance from the titanium nucleus. This means that due to screening by the inner electrons, the outermost electrons have a relatively low ionization potential and are easily removed to produce the ion, Ti $^4$. In this ion, there are no electrons in the outer electron orbitals and these orbitals are available for electron occupation by electrons from other atoms or groups of atoms having an excess or relatively high concentration of electrons. These are called electron donor groups or ligand-donor groups or simply ligands.

Once the orbitals for electrons become available, the ion can then undergo the process called hybridization. This means that, depending on the balance between the energy required to reorient the orbitals in space through appropriate combinations of orbitals and that regained through orbital overlap with the ligands; the size of the titanium ion compared to the ligand i.e., the radius ratio of the cation to anion or coordinating ligand atom; and the effective electronic charge on the titanium nucleus, a number of possibilities arise for hybridization. It turns out that the hybrid most favored for titanium (and many other transition metal-ions) is the hexacoordinate octahedron. This is shown schematically as follows:

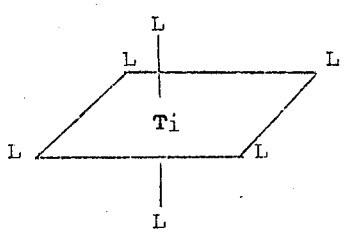

Each ligand donor group (designated L) is symmetrically located with respect to the central metal atom (titanium in this case). In this representation, all the ligands are implied to be the same. However, there exist many complexes in which they are not the same since the central metal atom is incapable of selecting only certain types of oxygen donor atoms over others.

An example of the nonselectivity of the central metal atom, (M), is the following: If it is supposed that the six ligand atoms are oxygen atoms and that of the six, two atoms come from source A, two from source B and two from source C, it is easy to conceive the schematic representation shown as follows:

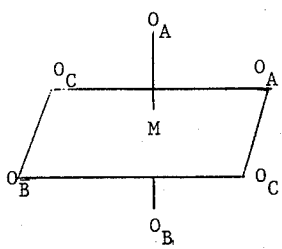

This is a gross oversimplification, but for the purposes of this explanation it is deemed valid.

If it is further supposed that source A is an organic molecule having the correct interatomic dimensions between oxygen atoms and that sources B and C are oxygen atoms belonging to either a glass fiber surface or to other titanium atoms nearby, the schematic representation shown in the FIGURE in the drawing can be envisioned. The practical result of this arrangement is a polymerized titanium oxide film on the fiber surface which is complexed with the organic ortho-dihydroxyphenyl molecule.

The factors governing the stability of such a complexed species are quite complicated, and in fact, it would be fairly difficult to predict the stability utilizing complex ion theory. Mechanistic organic chemistry however predicts that the stability of such complexes should be quite high for several reasons:

1. The entropy change associated with the formation of the five membered complex ring structure is quite large. Since the free energy of formation is enhanced, i.e., gains a larger negative value with the increase in entropy, a large probability of formation exists.
2. Hydrolytic stability or stability against disruption by nucleophilic species is precluded by conventional mechanisms of reaction due to the fact that all the ligand oxygen atoms are tied down firmly. This means that the formation of a transition state intermediate is impossible since the ligand atoms cannot move to accommodate the increased spatial requirements of such a state.
3. The molecule is not vulnerable to anything but electrophilic substitution reactions. The coordinated oxygen atoms of the ortho dihydroxyphenyl molecule cannot undergo any of the mechanistic reaction path ways for displacement. This is not true for the chromiumcarboxylato complexes in commercial use, i.e., Volan or "Quilon". The carbonyl function is very susceptible to nucleophilic attack.

Thus theoretical considerations predict that complex formation should not only occur (barring unforeseen complications) but also that the complex formed should be quite stable. Furthermore, as indicated in the single FIGURE of the drawing, there must also exist a definite stereo-chemical orientation of the organic portion of the complex. It can be seen in the FIGURE that the plane of the organic portion of the complex must be oriented at approximately 90° to the plane of the titanium oxide film. This fact has several interesting practical consequences:

1. If the effective area of the titanium oxide unit of the matrix is known, it should be possible to measure not only the surface area but also the surface roughness of the fiber.
2. It should also be possible to demonstrate the effect of this stereo-chemical orientation by complexing molecules of varying molecular dimensions.
3. If the ortho-dihydroxyphenyl portion of the molecule were modified with the appropriate chemical functional groups in the correct position, it should be possible to demonstrate "coupling action" in the appropriate chemical resin system.
4. It should be possible to firmly complex any desired chemical functionality to the fiber surface.

The hydrolytic stability and stereo-chemical relationship proposed were verified from test data obtained from heat cleaned, 621 glass fabric samples, that contained a titanium dioxide film that was complexed with catechol or Alizarin Red S. The hydrolytic stability of the complexes was evidenced by the fact that very little weight loss of the catechol and Alizarin Red S was noted after five hours immersion of the samples in water at 94° C.

Depending on the mechanism of bonding for the Alizarin Red S molecule, its molecular size will be 3 or 4 times larger than the smaller molecule catechol. Thus, it can be expected to occupy 3 or 4 times more area per molecule on the fiber surface. Since the fiber area remains essentially constant, the number of molecules required to occupy that area decreases correspondingly. Comparison of the "roughness factors" for the molecules studied shows that the average factor for catechol is 6 and the average for Alizarin Red S is 1.4. Their experimentally measured ratio is 4.3 which is slightly greater than the maximum of 4 predicted on the basis of molecular dimensions in the complexed state.

The stoichiometry of the complexes between titanium atoms and the ortho dihydroxy phenyl groups is that one atom of titanium complexes with one molecule of the ortho dihydroxy aromatic compound, i.e., a 1:1 complex. This is necessary to explain the hydrolytic stability required for the complex to serve as a coupling agent. The 1:1 complex permits the titanium atom to bond to other titanium atoms on the surface of the glass and to bond by hydrogen bonding to the surface of the glass. It therefore appears that in any of the complexes that are formed in the practice of the invention, there must be a minimum of three primary valences per metallic atom complexed in order to obtain a hydrolytically stable bond between the complex coupling agent and the substrate.

The invention is applicable to numerous types of substrates. The substrate can be siliceous in chemical nature, i.e., a silicate glass or a silica or silicate pigment. The glass can be in fibrous, flat or other form or shape, such as bottles, lenses, cathode ray tubes, laboratory glassware, etc. The preferred mode of performing the invention is described with regard to the use of 621 type glass fibers as the substrate, however, the applicability of the invention is not so limited. A 621 type glass is the commercial fiber glass composition that is described in U.S. Pat. No. 2,571,074.

DESCRIPTION OF THE PREFERRED EMBODIMENTS

EXAMPLE I

Separate solutions of the following are prepared:
1. An aqueous solution containing 0.5% by weight of isopropyltitanate (pH=2; 0.15% titanium ion)
2. An aqueous solution containing 0.1% by weight of catechualdehyde.
3. An aqueous solution containing 0.1% by weight of ethylene diamine.

A heat cleaned glass tape of 621 glass is dipped consecutively in solutions 1, 2 and 3. The tape is held immersed in each solution for 30 seconds before being withdrawn. The tape, after dipping, is dried at 110° C. for 10 minutes.

EXAMPLE II

The procedure of Example I is followed with the exception that solution 3 contains triethylene tetramine as the functional grouping on the dihydroxy compound.

EXAMPLE III

The procedure of Example II is followed with the exception that solution 2 contains αchloro-3,4-dihydroxy acetophenone as the dihydroxy phenyl compound.

EXAMPLE IV

The procedure of Example III is followed with the exception that solution 3 contains tetraethylene pentamine as the functional grouping on the dihydroxy phenyl compound.

EXAMPLE V

The procedure of Example IV is followed with the exception that solution 3 contains Polyamine D (molecular weight - 233) as the functional group. Polyamine D is a mixture of aliphatic and cyclic polyethylene amines manufactured and sold by Union Carbide Company.

The treated tapes in Examples I–V are tested for adhesion to rubber by first dipping the tape in the following rubber adhesive solution.

| Ingredients | Parts by Weight |
|---|---|
| Resorcinol | 340 |
| $CH_2O$ (37% aqueous solution) | 500 |
| NaOH | 4.65 |
| Butadiene - Styrene - Vinyl pyridine terpolymer latex (Gen-Tac - 41% solids dispersed in water) | 7565 |
| $NH_4OH$ (28% $NH_3$ in $H_2O$) | 350 |
| Deionized water | 6725 |
| Solids content (non aqueous) by weight | 23.4% |

The amount of adhesive picked up by the tape amounted to about 10–20% by weight of tape. The coated tape is then dried at 110° C. for 10 minutes.

The treated tape is then molded into a standard rubber stock under 20,000 pounds total pressure at 300° F. for 30 minutes. The rubber stock has the following composition (the chemical identification of the ingredients can be found in Materials and Compounding Ingredients for Rubber and Plastics published in Rubber World):

| Ingredients | SBR - Natural Rubber Blend |
|---|---|
| SBR 1500 | 75 |
| No. 1 RSS (Rubber smoked sheet) | 25 |
| HAF Black | 50 |
| ZnO | 5 |
| Stearic Acid | 1 |
| Age-Rite Resin (Antioxidant) | 1 |
| Sundex 790 (Plasticizer) | 10 |
| Santocure (Accelerative) | 1 |
| DOTG | 0.2 |
| Sulfur | 2.0 |

The results of these tests are as follows with the control tape sample being prepared as above-described but without the treatment of Examples I to V:

| Sample No. | | Average Adhesion (Pounds per one-half inch of tape) |
|---|---|---|
| 1. | Control | 2–4 |
| 2. | Example I | 10 |
| 3. | Example II | 16.9 |
| 4. | Example III | 27.8 |
| 5. | Example IV | 32.8 |
| 6. | Example V | 30.2 |

It is to be noted from the results of the tests that the higher boiling amines provide better adhesion when employed as the functional group in the coupling agent as prepared in Examples I to V. The lower weight polyamine molecules very likely volatilize from the tape before extensive reaction with the aromatic portion of the complex. Better results are obtained with the lower molecular weight amines when the coupling agent complex is completely formed prior to application to the tape.

An example of the coupling agent complex utilizing zirconium instead of titanium is set forth in Example VI.

EXAMPLE VI

Five milliliters of an aqueous solution of ammonium zirconyl carbonate containing 10% by weight of zirconium is prepared and diluted to 100 milliliters of solution by addition of water. To this solution is added consecutively with stirring until dissolved, 0.1 gram of α chloro-3,4-dihydroxy acetophenone and 0.1 gram of polyamine D. The resulting solution is yellow.

Heat cleaned, 621 glass fiber tape is dipped for about 30 seconds in the yellow solution, removed and dried at 130° C. for 10 minutes.

A rubber adhesive is prepared by dissolving 35.7 grams of a 70% by weight aqueous phenol-formaldehyde resole in 100 milliliters of water. To this is added 55 milliliters of concentrated ammonium hydroxide (28% by weight). The solution is allowed to react for about 15 minutes until the solution turns green. Next, 1.25 grams of resorcinol is added to the green solution with stirring until the resorcinol is dissolved and then 238 milliliters of water is added. To this mixture, is added 125 grams of Gen-Tac latex.

The previously treated glass fiber tape is dipped in the rubber adhesive for 30 seconds and removed to allow the excess to drip off. Approximately 10–20% by weight of adhesive is applied by this procedure. The adhesive coated tape is dried at 360° F. for 10 minutes. The tape is then molded into the standard rubber stock described above under 20,000 pounds total pressure at 300° F. for 30 minutes. The average adhesion obtained is 35.8 pounds per one-half inch of tape.

EXAMPLE VII

Two grams of α chloro-3,4-dihydroxy acetophenone are refluxed with 2.0 grams of p,p-diaminodiphenylmethane in 50 milliliters of methanol for one hour and then cooled to room temperature. Approximately 5 milliliters of the solution is added to 100 milliliters of a 0.5% by weight aqueous solution of $Cr^{+3}$ from chromium chloride (pH=2).

Heat cleaned, 621 glass fiber tape is dipped for about 30 minutes, in the above solution, shaken to remove excess solution and air dried.

A rubber adhesive is prepared by dissolving 300 grams of a 70% by weight phenol formaldehyde resole (Union Carbide BRL 1583-B.15) in 500 milliliters of water. To this is added 16 grams of ammonium thiocyanate. The resulting solution is diluted with 800 milliliters of water and 160 milliliters of 28% ammonium hydroxide is added. The solution is allowed to react for about 15 minutes until the solution turns green. To this green solution is added with thorough mixing, 1200 grams of equal parts Gen-Tac latex and Gen-Flo latex in 1000 milliliters of water.

The previously treated glass fiber tape is dipped in the rubber adhesive for about 30 seconds and removed to allow the excess to drip off. Approximately 10 to 20% by weight of adhesive is applied by this procedure. The adhesive coated tape is dried at 360° F. for 10 minutes. The tape is then molded into the standard rubber stock described above under 20,000 pounds total pressure at 300° C. for 30 minutes. The average adhesion obtained is 39.4 pounds per ½-inch of tape.

EXAMPLE VIII

The procedure of Example VII is repeated except that ferric nitrate is employed in place of chromic chloride. The average adhesion obtained is 32.1 pounds per ½-inch of tape.

EXAMPLE IX

A glass fiber strand forming size utilizing the complex coupling agent of the invention is prepared as follows:

A. Coupling Agent

Dissolve 0.1 mole of α chloro-3,4-dihydroxy acetophenone in 100 milliliters of methanol. Add this solution to 0.1 mole of ethylene diamine which is dissolved in 50 milliliters of methanol. The solutions are stirred with 0.005 mole of $Na_2CO_3$ and the NaCl formed is removed from the solution. Dissolve 0.1 mole of $TiCl_4$ in 200 milliliters of methanol and reflux this solution for 30 minutes. The compound which is thereby formed is $Cl_2Ti(OCH_3)_2$. Add the reaction mixture of $TiCl_4$ and methanol to the previously prepared solution and stir. An intense reddish-black complex is formed. The methanol is removed by vacuum evaporation, and a complex having the following diagrammatic structural formula is formed:

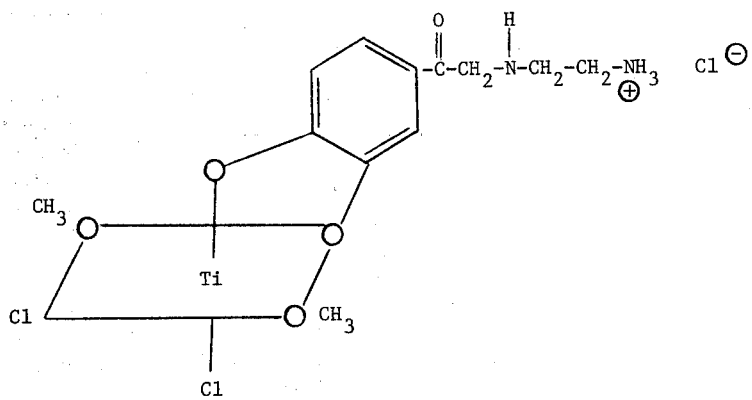

B. Ventromer 110

A 500 milliliter, four neck flask is fitted with a water cooled reflux condenser, an ice condenser and a dry ice condenser all connected in series. A thermometer and dropping funnel and stirrer are also fitted into the flask.

The flask is purged with dry nitrogen and charged with 200 grams of redistilled methylene chloride and 104 grams (2 moles) of redistilled methyl borate. Titanium tetrachloride is added dropwise over a period of about two hours, heat is evolved and yellow solids quickly form. When about half of the TiCl$_4$ has been added, methyl chloride starts to come off and is condensed out in the dry ice trap. When all of the TiCl$_4$ has been added, heat is applied to the flask to keep the methylene chloride refluxing. As methyl chloride is evolved, the yellow solids slowly disappear. Refluxing is continued for about 3.5 hours until no more CH$_3$Cl comes off and a homogeneous yellow solution is obtained. The maximum temperature reached during this reaction is about 56° C. There is collected about 54.3 grams of low boiling (−22° C.) liquid which analyzes to be about 95% and 5% dimethyl ether.

The homogeneous yellow solution is quite fluid at room temperature. However, as methylene chloride is vacuum evaporated, the solution becomes increasingly more viscous, reaching a taffy-like consistency and finally a glassy-like consistency. Final removal of methylene chloride is accomplished by heating to 65° C. under a vacuum of 10 millimeters of mercury for 24 hours. The yield of light yellow solid product is 141 grams, which analyzes as follows:

Ti= 17.2%; B= 7.5%; Cl= 24.8%; CH$_3$O= 39.4%
Ratios - Ti/B=1/1.9; Ti/Cl=1/2 B/OCH$^-_3$=1/1.8

The structural formula of the material formed is as follows:

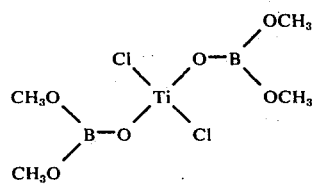

A forming size is prepared by mixing the following ingredients:

| Ingredient | Amounnt |
|---|---|
| Coupling agent-(A) | 20 grams |
| Ventromer 110-(B) | 80 grams |
| Nylon resin aqueous dispersion (30% by weight of polyamide) | 1500 grams |
| Water | Sufficient for 5 gallons of size |

The size is prepared by first mixing A and B in 2 1/2 gallons of water with stirring for 15 to 30 minutes to allow them to dissolve to form a clear red solution. The nylon dispersion is then dispersed in 2 gallons of water and added to the clear red solution. Water is then added to make 5 gallons of sizing solution.

The size is applied to the individual G-75 glass fibers during their formation in the conventional manner. The size is applied to the individual fibers just after their emergence from orifices in an electrically heated, platinum alloy bushing containing molten glass. The size is applied to the filaments prior to the time they are grouped together to form a strand by means of a roller applicator which is partially submerged in the size contained in a reservoir. Such an applicator is shown in more detail in U.S. Pat. No. 2,728,972. The fibers are grouped into a strand by a graphite guide and wound around a forming tube rotating at approximately 7500 r.p.m. to produce a strand travel of approximately 12,000 to 15,000 feet per minute. Other methods of applying the size to the strand of glass fibers, such as pad applicator, may be employed and the strand may be formed by means other than winding on the forming tube, such as by means of a pair of rotating wheel pullers which direct the strand into a suitable collecting device.

The glass fiber strands wound on the forming tube are then dried. This may be done by heating them at a temperature and for a length of time sufficient to reduce the moisture level to that appropriate for further processing, for example, at about room temperature for 48 hours for twisting or 8 to 12 hours at 270° F. for producing roving. This drying causes the coupling agents to fix themselves to the glass surface and to produce the degree of strand integrity and moisture level required for processing the strand into roving, yarn, cord, woven cloth or woven roving. The solids content of size on the strands averages about 0.2 to 2.0 per cent by weight, preferably about 0.50 per cent by weight.

The G-75 strand is twisted to form 0.5Z yarn and is coated with the rubber adhesive described in conjunction with the testing of the samples from Examples I to V so as to obtain about 17% by weight of adhesive when the coated yarn is dried. The adhesive is aged for 48 hours prior to application to the yarn. The coated yarn is dried in a dielectric oven and hot air oven in tandem. Five ends of coated and dried yarn are combined and twisted to form a 2.5S cord.

The cord is tested for properties as a reinforcement for the standard rubber stock described above. The test samples are prepared and tested as described above with the following results:

| | |
|---|---|
| Strip adhesion (pound per inch) | 54.4 |
| Scott flex life (cycles to failure) | 1.13 × 10$^6$ |
| "In-rubber" tensile (pounds per strand) | 15.5 |
| Cord Tensile (pounds per strand) | 12.1 |

EXAMPLE X

Glass fiber strand prepared as described in Example IX but without the rubber adhesive coating, is chopped to lengths of ¼ inch and combined with a commercial polyester resin premix compound. The resin when cured had improved dry and wet tensile strength compared to chopped strands sized with no coupling agent.

EXAMPLE XI

A G-37's strand is sized during forming as described above in Example IX with a size composed of the following ingredients:

| Ingredient | Weight |
|---|---|
| Ventromer 110 (titanium source) | 50 grams |
| PB-3-1521 Nylon dispersion (30%) | 1500 grams |
| Water | Sufficient to form 5 gallons of size |

The resulting forming packages are air dried for 48 hours. The strand is removed from the forming package and twisted to form 0.5Z yarn. The yarn is coated with a rubber adhesive, dried, and twisted as described in Example IX to produce a G-37's 5/0 2.5S tire cord. This cord is tested as in Example IX to give the following results.

| | |
|---|---|
| Strip adhesion (pounds per inch) | 70 |
| Scott flex life (cycles to failure) | 104,750 |
| Tensile in rubber (pounds per cord) | 121 |
| Tensile retention (%) | 103 |

Although the present invention has been described with respect to specific details of certain embodiments thereof, it is not intended that such details act as limitations upon the scope of the invention except insofar as set forth in the accompanying claims.

I claim:

1. An article of manufacture which comprises a siliceous substrate coated with a hydrolytically stable coordination compound of a transition metal oxide with an ortho-functional monoyclic aromatic compound in which the ortho substituents have unshared electrons in a 1:1 complex with the transition metal atom, said transition metal atom bonding by means of an oxygen atom to the other transition metal atoms on the surface of the siliceous substrate, the ortho-functional aromatic compound containing an additional functional organic group which is reactive with organic materials, said functional organic group selected from the class consisting of amine, imine, polyamine, polyimine, chloro-containing, thio-containing, olefinic-containing, epoxy-containing, or hydroxyl-containing and the ortho-functional aromatic compound when complexed with the metal oxide forms resultant 5, 6 or 7 membered rings.

2. An article as described in claim 1 in which the ortho substituents of the aromatic compound are hydroxyl radicals.

3. An article as described in claim 1 in which the substrate contains hydroxyl groups on its surface.

4. An article as described in claim 1 in which the substrate is fibrous.

5. An article as described in claim 1 in which the additional functional group is an amine resin.

6. An article as described in claim 1 in which the additional functional group is a polyamine.

7. An article as described in claim 1 in which the transition metal is titanium.

8. An article of manufacture which comprises an organic material which is reinforced with an article as described in claim 1.

9. An article as described in claim 8 in which the organic material is a resinous material.

10. An article of manufacture as described in claim 8 in which the organic material is an elastomer.

11. An article as described in claim 8 in which the organic material is an elastomeric adhesive.

12. An article as described in claim 1 which is coated with an organic material.

13. A method of coating a siliceous substrate having a film of a transition metal oxide thereon comprising:
    a. complexing on the surface of said siliceous substrate the said film of a transition metal oxide with an ortho-functional monocyclic aromatic compound in which the ortho substituents have unshared electrons to form a 1:1 complex, and
    b. heating the complexed substrate to render the complex hydrolytically stable, thus forming a coating on said siliceous substrate, the 1:1 complex permitting the transition metal atom to bond by means of an oxygen atom to other transition metal atoms on the surface of the siliceous substrate, the ortho-functional monocyclic aromatic compound when complexed with the transition metal oxide forms resultant 5, 6 or 7 membered rings and the ortho-functional monocyclic aromatic compound also containing an additional functional group which is reactive with organic materials, said functional organic group selected from the class consisting of amine, imine, polyamine, polyimine, chloro-containing, thio-containing, olefinic-containing, epoxy-containing or hydroxyl-containing.

14. A method as described in claim 13 in which the ortho substituents of the aromatic compound are hydroxyl radicals.

15. A method as described in claim 13 in which the additional functional organic group is a polyamine.

16. A method as described in claim 13 in which the substrate is fibrous.

17. A method as described in claim 13 in which the transition metal is titanium.

18. A method of coating a siliceous substrate having a film of a transition metal oxide thereon consisting of:
    a. complexing at the surface of said siliceous substrate the said film of a transition metal oxide with an ortho-functional phenolic or resorcinolic resin in which the ortho substituents have unshared electrons to form a 1:1 complex, and
    b. heating the complexed substrate to render the complex hydrolytically stable, thus forming a coating on said siliceous substrate, the 1:1 complex permitting the transition metal atom to bond by means of an oxygen atom to other transition metal atoms on the surface of the siliceous substrate, and the ortho-functional phenolic or resorcinolic resin when complexed with the transition metal oxide forms resultant 5, 6 or 7 membered rings.

19. A method as described in claim 18 in which the substrate is fibrous.

20. A method as described in claim 18 in which the transition metal is titanium.

* * * * *

UNITED STATES PATENT OFFICE
CERTIFICATE OF CORRECTION

Patent No. 3,993,835      Dated November 23, 1976

Inventor(s) Patrick M. Miedaner

It is certified that error appears in the above-identified patent and that said Letters Patent are hereby corrected as shown below:

Column 2, line 33, "singe" should be --single--.

Column 3, title phrase, "Brief Description of the Figures" should be --Brief Description of the Drawing--.

Column 3, line 30, "exmple" should be --example--.

Column 4, line 15, "ore" should be --or--.

Column 4, line 55, "$Ti^4$" should be --$Ti^{+4}$--.

Column 13, line 25, "monoyclic" should be --monocyclic--.

Signed and Sealed this

Twelfth Day of April 1977

[SEAL]

Attest:

RUTH C. MASON
Attesting Officer

C. MARSHALL DANN
Commissioner of Patents and Trademarks